United States Patent [19]

Marino, Jr. et al.

[11] Patent Number: 4,634,434
[45] Date of Patent: Jan. 6, 1987

[54] APPARATUS FOR REGULATING THE FLOW OF FLUID IN MEDICAL APPARATUS

[75] Inventors: Joseph A. Marino, Jr., Apple Valley; Matthew E. Bellin, Burnsville, both of Minn.

[73] Assignee: Biomedical Dynamics Corporation, Burnsville, Minn.

[21] Appl. No.: 702,991

[22] Filed: Feb. 19, 1985

[51] Int. Cl.⁴ ............................................. A61M 5/005
[52] U.S. Cl. .................................. 604/246; 604/249; 138/46; 251/126
[58] Field of Search ............. 604/30, 32, 33, 246–250, 604/256, 241; 251/126–128, 215–217, 296, 297, 229, 334; 138/40, 43, 45, 46

[56] References Cited

U.S. PATENT DOCUMENTS

| | | | |
|---|---|---|---|
| 982,106 | 1/1911 | Thornycroft. | |
| 1,723,066 | 8/1929 | Ogden | 251/215 |
| 2,105,314 | 1/1938 | Duncan et al. | 137/104 |
| 2,323,115 | 6/1943 | Bryant | 138/43 |
| 2,698,160 | 12/1954 | Hansen | 251/229 |
| 2,752,201 | 6/1956 | Blass | 299/106 |
| 3,069,126 | 12/1962 | Randall | 251/126 |
| 3,091,213 | 5/1963 | Maskell et al. | 116/70 |
| 3,143,145 | 8/1964 | Kauss | 138/43 |
| 3,840,209 | 10/1974 | James | 251/216 |
| 3,841,354 | 10/1974 | McDonnell | 251/126 |
| 3,907,249 | 9/1975 | Persson | 251/126 |
| 3,998,244 | 12/1976 | Bentley | 138/43 |
| 4,027,669 | 6/1977 | Johnston et al. | 604/241 |
| 4,044,834 | 8/1977 | Perkins | 166/314 |
| 4,044,991 | 8/1977 | Waller | 251/122 |
| 4,079,737 | 3/1978 | Miller | 604/248 |
| 4,176,683 | 12/1979 | Leibinsohn | 137/559 |
| 4,240,424 | 12/1980 | Akhavi | 604/241 |
| 4,432,762 | 2/1984 | Dawe | 604/253 |

FOREIGN PATENT DOCUMENTS 1126735  11/1956  France ............................. 251/126

Primary Examiner—Dalton L. Truluck
Assistant Examiner—Mario Costantino
Attorney, Agent, or Firm—Kinney & Lange

[57] ABSTRACT

A flow regulator for use in medical apparatus for adjusting the flow of fluid in which there is a valve body with a valve member having a helical flow passage through which the fluid must flow. In order to facilitate quick adjustment of the fluid, the pitch and depth of the groove both progressively change from one end of the flow regulating device to the other, the depth of the groove becoming less as the pitch of the groove becomes finer. The valve member is longitudinally movable with respect to the valve body, and provision is made for adjusting the longitudinal position either by rotation of a threaded valve stem or by longitudinal movement of the valve stem to quickly adjust the flow rate. The helical groove may be either rectangular in cross-section, or V-shaped in cross-section. Suitable means are provided for sealing against leakage through the valve adjusting means.

10 Claims, 5 Drawing Figures

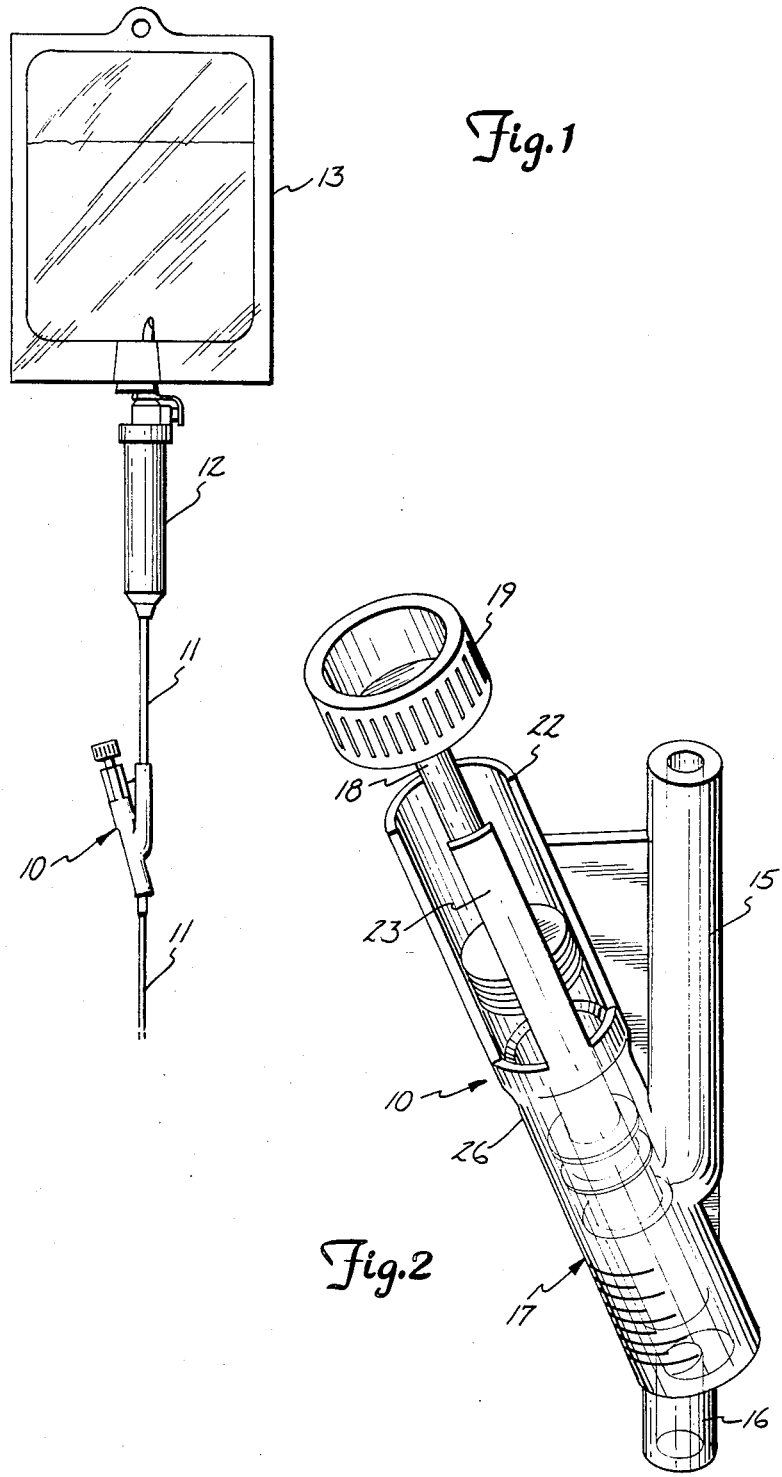

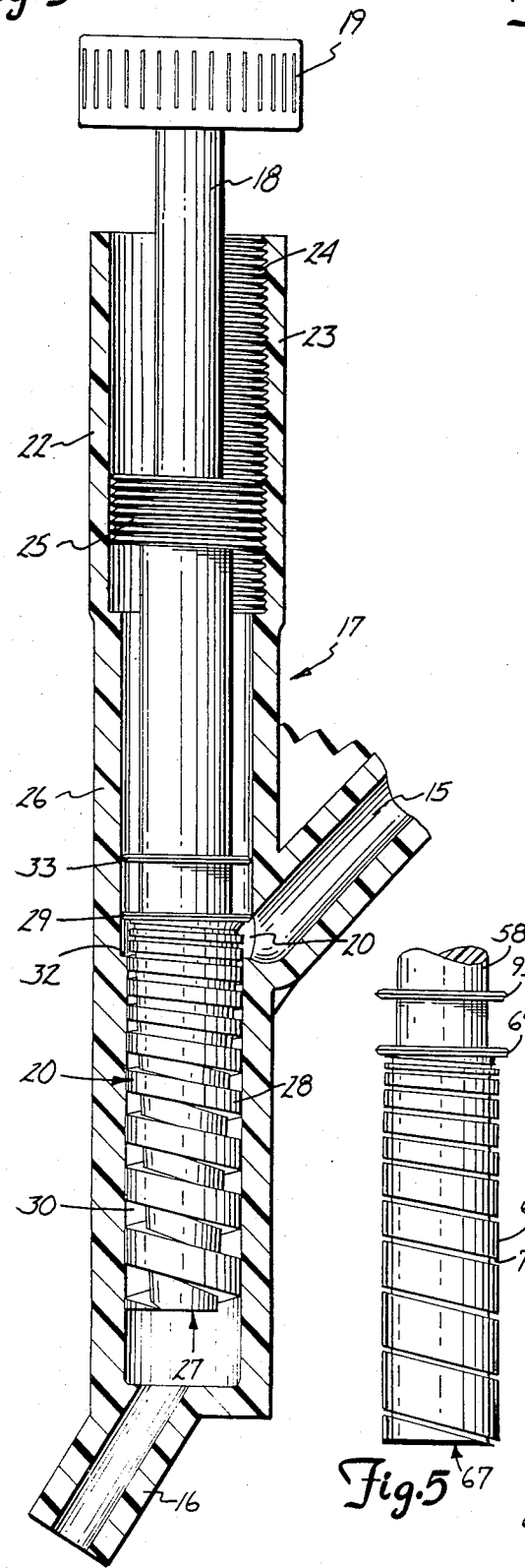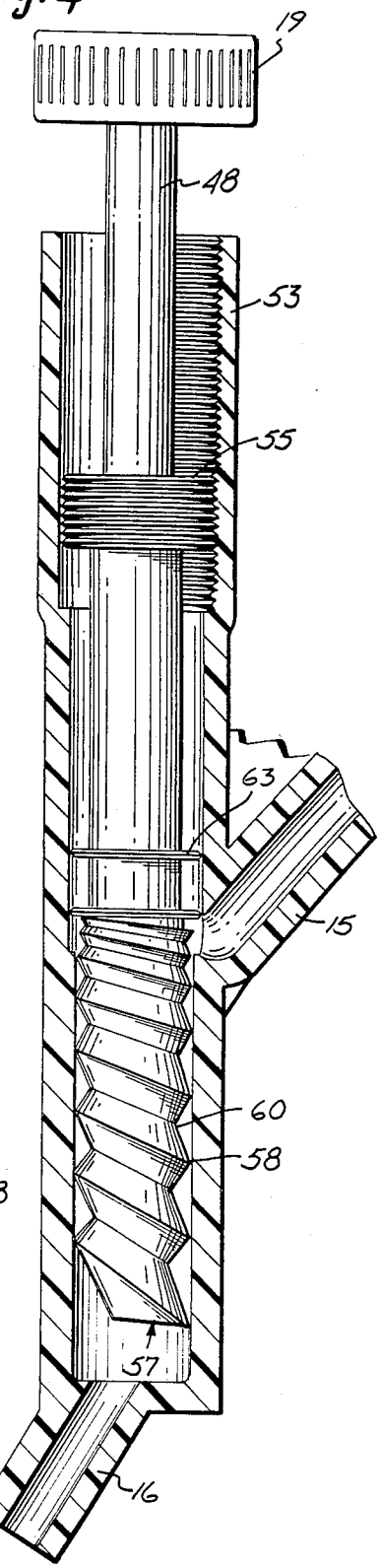

APPARATUS FOR REGULATING THE FLOW OF FLUID IN MEDICAL APPARATUS

BACKGROUND OF THE INVENTION

1. Field of the Invention

The present invention is concerned with a device for regulating the flow of fluid in medical apparatus in which there is a valve member having a helical passage for flow of the fluid.

2. Description of the Prior Art

There are many applications in medical equipment in which it is necessary to adjust the flow of fluid. Moreover, the adjusting means usually has to be relatively compact. A typical application is in connection with intravenous feeding in which the fluid from a container designed to hold the intravenous fluid is connected by a tube or other flexible conduit to means for introducing the fluid into the patient. Any means for regulating the flow of such fluid must be very compact and must be capable of quickly adjusting the flow of fluid. It also must be capable of adjusting it in very small increments so that the flow rate is exactly what is desired.

The conventional way of adjusting flow of fluid in such apparatus is through a roller flow control clamp. This is referred to in the Dawe U.S. Pat. No. 4,432,762. The difficulty with this type of arrangement is that it is very difficult to effect accurate adjustment and there is a great tendency for the adjustment to shift once it has been set.

This problem is recognized in the McDonnell U.S. Pat. No. 3,841,354 in which there is a male member in threaded connection with a female member, the threads of the male member being less in height than the depth of the grooves in the female member so that there is a passage between the male and female threads. Furthermore, McDonnell suggests varying the depth of the grooves to provide further adjustment. In such a case, the fluid travels helically in the space between the threads. McDonnell specifically is concerned with an arrangement for adjusting the flow of intravenous fluids. The McDonnell device is, however, of a type which requires relatively slow adjustment and, if one wishes to make a major adjustment of the rate of flow, it is necessary to move the movable valve member through a large number of turns.

Various arrangements have been proposed for metering fluid in which a helical fluid channel is employed. Among such patents are the Duncan et al U.S. Pat. No. 2,105,314. In this patent, the threads of the movable male member slidably engage the wall of the female member so that it is possible to move the male valve member longitudinally to effect quick changes in flow. It is impossible, however, to effect accurate minute adjustments. Furthermore, the rate of change of flow is uniform throughout the movement of the valve member.

The Bryant U.S. Pat. No. 2,323,115 also shows an arrangement in which there is a helical passage and in which, in one modification, the depth of the groove progressively varies from one end to the other. There is no suggestion, however, of varying the pitch of the space to obtain additional variation in change of flow.

Other patents which show helical groove flow regulating devices are the Thornycroft U.S. Pat. No. 982,106, the Maskell et al U.S. Pat. No. 3,091,213, the Blass U.S. Pat. No. 2,752,201, the Kauss U.S. Pat. No. 3,143,145, the Persson U.S. Pat. No. 3,907,249, the Bentley U.S. Pat. No. 3,998,244, the Perkins U.S. Pat. No. 4,044,834, the Waller U.S. Pat. No. 4,044,991, and the Leibinsohn U.S. Pat. No. 4,176,683. While all of these arrangements show the flow regulating device in which there is a helical groove the relative length of which is adjusted, none of them are concerned with extremely compact units and none of them are concerned with varying the pitch to obtain added change in the length of the helical path per unit of longitudinal movement of the flow regulating member.

SUMMARY OF THE INVENTION

The present invention is concerned with a flow regulating device particularly designed for use in medical apparatus in which there is a flow regulating member having a helical groove portion on the exterior thereof to form a helical fluid passage between the inlet and outlet openings with the pitch of the helical groove varying through at least a portion of the extent of the flow regulating member.

In the device of the present invention, the helical groove is disposed upon a longitudinal flow regulating member, and means are provided for moving the member longitudinally to vary the amount of the helical passage disposed between the inlet and outlet openings of the flow regulating device. This means for moving the flow regulating member longitudinally can move the flow regulating member in very small increments. For example, the means for adjusting the position of the longitudinal member may take the form of a screw-threaded arrangement which results in longitudinal movement of the flow regulating member when the stem of the screw-threaded arrangement is rotated. Provision may also be made for adjusting the flow regulating member longitudinally at a rapid rate. This may, for example, take the form of an arrangement in which a portion of the threaded connection between the valve housing and the stem is yieldable to permit the stem to move the flow regulating member longitudinally at a rapid rate. This is particularly desirable in connection with medical apparatus in which it is desirable to make the major adjustment of the fluid flow as rapidly as possible. In order to make the change in fluid flow as great as possible, the helical groove not only varies in pitch but also in the depth of the groove. As the pitch narrows, the depth of the groove is likewise decreased.

The flow regulating means is preferably provided with some means at one end for engaging a valve seat to completely shut off the flow of fluid. The point of finest pitch and cross-sectional area of the groove occurs at the end at which the flow regulating member engages the valve seat. Thus, as the flow regulating member is moved in the direction of the valve seat, the resistance to flow of the fluid is increased in three ways. In the first place, the total amount of the helical groove disposed between the inlet and outlet is increased. In the second place, the number of turns of the groove is increased to a greater extent than if the pitch was uniform. In the third place, by reason of the decreased volume of the channel formed by the helical groove, the resistance to flow of fluid is further increased.

Various other objects and features of the invention will be apparent from a consideration of the accompanying specification, claims and drawing.

BRIEF DESCRIPTION OF THE DRAWINGS

FIG. 1 is a view showing the improved flow regulating device connected into the tubing leading from a bag containing an intravenous fluid.

FIG. 2 is a perspective view of the improved flow regulating device.

FIG. 3 is a longitudinal sectional view of the flow regulating portion of the flow regulating device of FIG. 2.

FIG. 4 is a view similar to FIG. 3 showing another modification of the flow regulating device.

FIG. 5 is a elevational view of the flow regulating portion of a modified flow regulating device.

DETAILED DESCRIPTION OF THE PREFERRED EMBODIMENTS

Referring to the drawing, the numeral 10 is employed to generally indicate the flow regulating device of the present invention. It will be noted that this is connected in tube 11 which is connected through the usual drip counter 12 to a container 13 which may contain a suitable intravenous fluid.

Referring to FIG. 2, the flow regulating device is provided with a tubular intake member 15 which connects with the portion of the tube 11 leading to the drip counter 12. The flow regulating device is also provided with a tubular outlet member 16 which connects to the portion of the tube 11 leading to the device for administering the fluid to the body. This may take the form of a hypodermic needle (not shown). Interposed in a flow regulating manner between the inlet and outlet tubular members 15 and 16 is a flow regulating member 27 which is shown in more detail in FIG. 3. The flow regulating member is adjusted by a stem 18 to which is secured a knob 19.

Referring now to FIG. 3, it will be noted that the valve stem extends into a housing 17. As will be noted from FIG. 3, this housing is a basically cylindrical housing having a lower portion in which is disposed the flow regulating member 27 of the present invention. The upper portion of the housing 17 has a portion 22, cylindrical in shape but extending only partially around the circumference of the housing, as best seen in FIG. 2. As will be noted in FIGS. 2 and 3, this portion has no internal threads. The upper portion of the housing also has an upstanding, cylindrically curved member 23 which is internally threaded, as at 24. A stem 18 is provided with a collar 25 which has external threads engaging the internal threads 24 of the cylindrically curved portion 23. As will be best seen in FIG. 2, the cylindrically internally threaded curved portion 23 is in the form of an arm which extends upwardly from a central portion 26 of the housing to the top of the housing. Normally, the threaded collar 25 is in engagement with the threads 24, and by rotation of the knob 19 the stem 18 can be moved up or down. The threaded arm 23 is slightly yieldable and if sufficient horizontal force is applied to the knob 19, the stem 18 can be forced downwardly or upwardly by the threads of the threaded collar 25 slipping over the threads 24 of the threaded arm 23. As will be explained, this enables rather quick adjustment of the flow regulating member.

The flow regulating member 27 is secured to the lower end of the stem 18. The flow regulating member has a helical rib 28 running from the lower end to a shoulder portion 29. A groove 30 is formed by the helical rib 28. As will be apparent from FIG. 3, the pitch of the rib 28 becomes finer as the helical rib progresses from bottom to top. Furthermore, the depth of the groove 30 decreases from the lower end to the upper end of the flow regulating member 27. It will also be noted that the exterior diameter of the rib 28 is constant. In other words, the difference in depth of the channel between the turns of rib 28 is obtained by leaving more material at the base of the groove. This is important since it is desirable that the exterior surface of the helical rib 28 be that of a cylinder of uniform diameter so that it is possible to readily move the flow regulating member 27 up or down within the cylindrical wall of the housing 17.

The shoulder portion 29 of the stem 18, previously referred to, is adapted to seat upon an internally extending shoulder 32 of the housing 17. The shoulder 29 constitutes a valve member and the shoulder 32 a valve seat. If desired, a suitable resilient material may be secured to the stem adjacent the valve shoulder 29 so as to form a tighter seal when the shoulder 29 is moved into engagement with the internally extending shoulder 32 of the valve housing.

It will be readily apparent that fluid entering through the intake member 15 from the tube 11 leading to the bag containing intravenous fluid passes around the helical groove 30 and out through the bottom of the housing 17 through the outlet member 16. With the elements in the position shown in FIG. 3, the fluid passes around the helical groove through substantially its entire extent before passing out through the outlet member 16. If the knob 19 is rotated to move the stem 18 downwardly, the length of the helical groove 30 through which the fluid must travel is increased. If the knob is rotated until the valve head 29 engages the valve seat shoulder 32, the flow of fluid will be completely cut off. As the knob 19 is rotated in the opposite direction to raise the stem 18, the length of the helical channel 30 through which the fluid must flow is decreased. When the lowermost portion of the groove 30 is adjacent the tubular intake member 15, the fluid has to travel through only a very short helical channel which helical channel is of relatively large cross-section.

When it is desired to quickly adjust the flow, the knob 19 is pushed downwardly to push the stem 18 downwardly to quickly adjust the position of the flow regulating member with respect to the opening 20 from tube 15. In this way, it is possible to quickly move the flow adjusting member to the approximate position desired. Similarly, if the valve is substantially shut off by engagement of the valve head shoulder 29 with the valve seat shoulder 32, the knob 19 can be pulled upwardly springing the threads of the threaded collar 25 past the threads 24 until the flow regulating member is in the approximate position. Thereafter, rotation of the knob 19 can adjust the flow regulating member precisely to obtain the exact desired rate of flow.

While an opening exists between the upstanding arm 23 and the curved portion 22 of the upper portion of the housing 17, escape of fluid through this opening is prevented by a sealing ring 33 secured to the stem 18 and in sliding engagement with the interior wall of the central portion 26 of the housing 17. This sealing ring 33 can take any of various forms as long as it effectively forms a seal between the stem 18 and the interior wall of housing 17. Thus, any fluid that escapes past the shoulder portion 29 is blocked by the sealing ring 33 and cannot escape between the curved portion 22 and the arm 23 of the housing 17.

Because of the change of pitch of the groove 30, the change in depth of the groove 30, and the means for varying the extent of the groove disposed between the inlet opening 20 and the outlet, the fluid is varied in three ways. In the first place, the length of the helical channel is varied by reason of the extent of the helical channel between the inlet opening and the outlet opening. In the second place, the length of the helical channel is further varied by reason of the change in pitch of the groove 30. As one approaches closed position, the length of the turn progresses at a greater than linear rate. Lastly, the decreasing cross-sectional area of the groove 30 results in a still further change in the resistance to flow of fluid through the helical channel. The result of this is that it is possible to make a very substantial adjustment of the flow with very little movement of the knob 19. If the pitch of the groove 30 were uniform throughout the length, it would be necessary to move the stem 18 a greater distance to effect the same change in the flow as is obtained in the present device with a much smaller movement of the stem 18. The advantage of being able to make a very rapid change in the fluid flow with relatively small movement of the stem 18 is very important in the medical field. It is highly desirable that the rate of flow can be quickly adjusted. In the present device, it is possible to quickly move the flow regulating device to obtain approximately the desired flow and thereafter to make a very fine adjustment by simple rotation of the knob 19. Furthermore, because of the change in pitch and change in the depth of the groove 30, it is possible to have a much shorter unit than would otherwise be necessary. If the pitch and depth of the groove were uniform throughout, a greater length of adjustment of the stem 18 would be required. By changing the pitch and changing the depth of the groove, it is possible to make the apparatus much more compact. This is particularly important in the medical field.

It will also be noted that the pitch of the groove 30 and the cross-sectional volume of it is smallest adjacent the valve head shoulder 29. This is important because as one approaches closed position, it is desirable to restrict more and more the flow of the fluid until finally the valve shoulder engages the valve seat to completely cut off the flow.

MODIFICATION OF FIG. 4

The modification of FIG. 4 is similar to that of FIG. 3, with the exception that the grooves instead of being rectangular in cross-section, are V-shaped in cross-section. In order to enable a ready comparison of the FIGS. 3 and 4, the elements in FIG. 4 corresponding to elements in FIG. 3 have been designated by reference numerals thirty higher than those applied to the corresponding elements in FIG. 3. For example, the stem is designated with reference numeral 48, the upstanding threaded arm by the reference numeral 53, the threaded collar by the reference numeral 55, the sealing ring by the reference numeral 63, and the flow regulating member generally by the reference numeral 57. The groove in this Figure is designated by the reference numeral 60, and the rib is designated by the reference numeral 58. It will be noted that the groove 60 in this case varies both in pitch and in depth, just as in FIG. 3. The difference, however, is that the groove 60 is V-shaped in cross-section. In some cases, this has an advantage in that the flow may be less turbulant than in a channel of rectangular cross-section. The arrangement of FIG. 4 has the same advantage as that of FIG. 3 and functions in the same manner. As with the arrangement of FIG. 3, the adjustment of flow can be initially made very quickly. Thereafter, a very fine adjustment of the flow can be made.

MODIFICATION OF FIG. 5

The modification of FIG. 5 is similar to that of FIGS. 3 and 4 with the exception that the helical groove through which the fluid flows varies only in pitch and not in depth. In order to enable a comparison of the elements of FIG. 5 with those of FIGS. 3 and 4, the elements have been given numerals forty higher than the corresponding elements in FIG. 3. Thus, the groove is indicated by the reference numeral 70, and the rib formed by the groove 70 is indicated by the reference numeral 68. It is to be understood that the groove may have other cross-sectional configurations, not shown, such as being semi-circular in cross-section. It will be readily apparent from an examination of FIG. 5 that the groove 70 varies in pitch from the bottom of the flow regulator 67 to the top, the pitch of the groove becoming progressively finer. The difference is that the groove 70 is of constant depth throughout.

The arrangement of FIG. 5 does not give as rapid a change in adjustment of fluid flow as is possible with the arrangements of FIGS. 3 and 4. It has the advantage, however, that it is simpler to machine and easier to fabricate. At the same time, it does give very substantial adjustment in the flow rate for a given longitudinal movement of the flow regulating member 67.

CONCLUSION

It will be seen that we have provided a flow regulating device in which it is possible to make a very substantial adjustment of the flow with a relatively small movement of the flow regulating member. Furthermore, because of the fact that the valve stem not only can be rotated to adjust the flow regulating device very finely, but it can also be moved longitudinally to make quick adjustments.

While we have shown certain specific embodiments of our invention, it is to be understood that this is for purpose of illustration only and that the scope of our invention is limited solely by that of the appended claims.

What is claimed is:

1. For use in regulating the flow of a fluid in medical apparatus,
    a valve body having inlet and outlet openings and having a cylindrical passage therebetween defined by a cylindrical wall;
    a flow regulating member extending into the cylindrical passage and having an outer cylindrical surface closely engaging the wall of the cylindrical passage, the flow regulating member having a helical grooved portion on the outer cylindrical surface thereof to form a helical fluid passage through the outer body between said inlet and outlet openings, the pitch of the helical groove progressively varying over the extent of the groove; and
    actuating means for shifting the flow regulating member axially to vary the amount of the helically grooved portion that is disposed between the inlet and outlet openings to vary the length of the helical passage through which fluid must flow.

2. The apparatus of claim 1 in which the depth of the helical groove decreases as the pitch becomes finer so that the cross-sectional area of the helical passage decreases as the length of the helical passage per unit of linear length of the flow regulating member increases.

3. The apparatus of claim 1 in which there is means for enabling the outer cylindrical surface of said flow regulating member to be longitudinally slidable with respect to the wall of the cylindrical passage so that the flow regulating member can be axially moved by the actuating means for quick adjustment of the length of the helical passage through which fluid must flow.

4. The apparatus of claim 1 in which sealing means is disposed between the actuating means and the flow regulating member to prevent fluid from said flow regulating member passing out through said actuating means.

5. The apparatus of claim 1 in which the flow regulating member has a stem projecting outwardly from the valve body and in which the actuating means includes coacting threaded portions on the valve body and the stem to cause change in the longitudinal position of the flow regulating member upon rotation of the stem.

6. The apparatus of claim 5 in which the threaded portion of the valve body has a plurality of parts, one of which is yieldable to permit quick change in the longitudinal position of the flow regulating member without rotation of the stem.

7. The apparatus of claim 2 in which the valve body has a valve seat therein between the inlet and outlet passages and the flow regulating portion has a valve portion adapted to engage the valve seat to shut off flow completely and in which the portion of the flow regulating member having the smallest depth and the finest pitch is adjacent the valve portion of the flow regulating member.

8. In combination with a container for intravenous fluid for delivering the fluid at a controlled rate to a patient, a flexible conduit extending from said container for delivery of said fluid, a valve in said conduit for adjusting the rate at which fluid is delivered, said valve comprising:

a valve body having inlet and outlet openings and having a cylindrical passage therebetween defined by a cylindrical wall;

a flow regulating member extending into the cylindrical passage and having an outer cylindrical surface closely engaging the wall of the cylindrical passage, the flow regulating member having a helical grooved portion on the outer cylindrical surface thereof to form a helical fluid passage through the valve body between said inlet and outlet openings, the pitch of the helical groove progressively varying from one end of the helical groove to the other; and actuating means for shifting the flow regulating member axially to vary the amount of the helically grooved portion that is disposed between the inlet and outlet openings to vary the length of the helical passage through which fluid must flow to adjust the flow of fluid from said container.

9. The apparatus of claim 8 in which the flow regulating member has a stem projecting outwardly from the valve body through an opening therein, in which the actuating means includes coacting threaded portions on the valve body and the stem to cause longitudinal shifting of the flow regulating member upon rotation of the stem, and in which there is a manually operable knob secured to the stem for rotation of the stem by the person administering the delivery of the intravenous fluid.

10. The apparatus of claim 9 in which the threaded portion of the valve body has a plurality of parts, one of which is yieldable to permit quick change in the longitudinal position of the flow regulating member without rotation of the stem to quickly adjust the delivery of the intravenous fluid.

* * * * *